United States Patent [19]
Espitalie et al.

[11] Patent Number: 5,958,777
[45] Date of Patent: Sep. 28, 1999

[54] DEVICE FOR DETERMINING $CO_2$ AND CO IN A GEOLOGIC SEDIMENT

[75] Inventors: Jean Espitalie, Le Vesinet; Francois Marquis, Montlignon, both of France

[73] Assignee: Institut Francais du Petrole, France

[*] Notice: This patent is subject to a terminal disclaimer.

[21] Appl. No.: 09/017,714

[22] Filed: Feb. 5, 1998

Related U.S. Application Data

[62] Division of application No. 08/727,344, Oct. 7, 1996, Pat. No. 5,811,308.

[30] Foreign Application Priority Data

Oct. 5, 1995 [FR] France .................................. 95 12001

[51] Int. Cl.$^6$ .................................................. G01N 31/12
[52] U.S. Cl. .................. 436/32; 436/25; 436/28; 436/29; 436/30; 436/31; 436/139; 436/140; 436/141; 436/143; 436/145; 436/146; 436/147; 436/149; 436/150; 436/154; 436/155; 436/157; 436/158; 422/54; 422/78; 422/80; 422/82.05; 422/93
[58] Field of Search .................. 436/25, 29, 28, 436/30, 31, 32, 139, 140, 141, 143, 145, 146, 147, 149, 150, 154, 155, 157, 158; 422/54, 78, 80, 82.05, 93

[56] References Cited

U.S. PATENT DOCUMENTS

| | | | |
|---|---|---|---|
| 3,953,171 | 4/1976 | Espitalie et al. | 422/82.05 |
| 4,153,415 | 5/1979 | Espitalie et al. | 23/230 EP |
| 4,213,763 | 7/1980 | Madec et al. | 23/230 EP |
| 4,229,181 | 10/1980 | Espitalie et al. | 23/230 EP |
| 4,352,673 | 10/1982 | Espitalie et al. | 23/230 EP |
| 4,519,983 | 5/1985 | Espitalie et al. | 422/78 |
| 4,837,158 | 6/1989 | Toulhoat et al. | 23/230 EP |
| 5,786,225 | 7/1998 | Lafargue et al. | 436/147 |
| 5,811,308 | 9/1998 | Espitalie et al. | 436/145 |

*Primary Examiner*—Jill Warden
*Assistant Examiner*—S. Carrillo
*Attorney, Agent, or Firm*—Millen, White, Zelano & Branigan, P.C.

[57] ABSTRACT

A device for determining at least one petroleum characteristic of a geologic sediment sample placed in a boat, said device including a first heater heating said sample in a non-oxidizing atmosphere, a measuring component determining hydrocarbon-containing products released after feeding the sample into said first heater, a second subsequent heater heating said sample in an oxidizing atmosphere, a measuring component determining the amount of $CO_2$ contained in effluents discharged from the two heaters, said $CO_2$ measuring means include a cell for measuring continuously $CO_2$ throughout heating of the first and second heaters and a measuring component determining the amount of CO contained in the effluents discharged from the two heaters, and thereby allowing determination of said petroleum characteristic.

11 Claims, 4 Drawing Sheets

FIG.4

DEVICE FOR DETERMINING $CO_2$ AND CO IN A GEOLOGIC SEDIMENT

This application is a divisional application of Ser. No. 08/727,344, filed Oct. 7, 1996, now U.S. Pat. No. 5,811,308.

FIELD OF THE INVENTION

The present invention relates to a method and to an improved device for determining at least some of the petroleum characteristics of a geologic sediment, such as for example, but not exclusively, the possibility of producing petroleum immediately or in the future, i.e. of being a good mother rock, or of being a reservoir rock containing hydrocarbons.

The present invention relates to an improvement of the ROCKEVAL technique (trademark registered by Institut Frangais du Pétrole) and an optimizaton of the measuring device for implementing the method. The prior ROCKEVAL technique is described in documents FR-2,339,173 and FR-2,472,754.

BACKGROUND OF THE INVENTION

The prior method and devices do not allow to measure $CO_2$ continuously during heating cycles: pyrolysis or oxidation. Furthermore, the CO that is released simultaneously with $CO_2$ cannot be measured. This analysis of the CO that is produced only by cracking organic matter is notably essential for an improved determination of the total organic carbon. This analysis allows, for example, to obtain a more precise oxygen index OI by including in the $CO_2$ the CO thus analyzed Simple interpretation in combination of the continuous CO and $CO_2$ curves allows the organic oxygen to be differentiated from the inorganic oxygen.

SUMMARY OF THE INVENTION

The present invention thus relates to a method for determining at least one petroleum characteristic of a geologic sediment sample, where the sample is heated in a non-oxidizing atmosphere, the temperature thereof being raised successively to a first, then to a second value, said first value, below 200° C., being reached very quickly and maintained substantially constant for some time, said second value ranging between 600 and 850° C. being reached with a temperature gradient ranging between 0.2 and 50° C./min, from said first value. According to the invention, the amount of $CO_2$ contained in the effluent resulting from heating of the sample is measured continuously throughout said period or heating of said sample, a curve representative of said amount of $CO_2$ can be drawn and the $CO_2$ of organic origin can be differentiated from the $CO_2$ of inorganic origin from continuous measurements and notably from the shape of the curve.

The amount of CO contained in the effluent resulting from heating of the sample can be measured continuously throughout said period of heating of said sample, and a curve representative of said amount of CO can be drawn.

The organic oxygen can be differentiated from the inorganic oxygen by combined interpretation of the continuous measurements and notably by means of the $CO_2$ and CO curves.

According to the method, the residues resulting from said heating in a non-oxidizing atmosphere are placed in another oven where they are heated in an oxidizing atmosphere, the temperature of the oxidizing atmosphere heating can be programmed so as to rise from a temperature of about 400° C. to an end temperature of about 850° C. with a temperature gradient ranging between 10 and 30° C./min. The amount of $CO_2$ contained in the effluent resulting from heating of said residues can be measured continuously throughout said heating period. A curve representative of said amount of $CO_2$ can be drawn and the $CO_2$ of organic origin can be differentiated from the $CO_2$ of inorganic origin from tide continuous measurements and notably from the shape of said curve.

The amount of CO contained in the effluent resulting from said heating of said residues can be measured continuously throughout the period of heating in an oxidizing atmosphere and a curve representative of said amount of CO can be drawn.

The amount of total organic carbon contained in said sample can be calculated from the continuous measurements and notably from the $CO_2$ and CO curves obtained after heating cycles in a non-oxidizing and an oxidizing atmosphere.

The invention further relates to a device for determining at least one petroleum characteristic of a geologic sediment sample placed in a boat, the device comprising a first means for heating said sample in a non-oxidizing atmosphere, means for measuring the amount of hydrocarbon-containing products released after feeding the sample into said fit heating means, a second means of heating in an oxidizing atmosphere, means for measuring the amount of $CO_2$ contained in the effluents discharged from the two heating means. The $CO_2$ measuring means include a cell for measuring continuously the $CO_2$ throughout the heating cycle of the first and of the second heating means, and means for measuring the amount of CO contained in the effluents discharged from the two heating means.

The first and the second heating means can each comprise an identical oven and means for programming the heating temperature of the two ovens.

The ovens can comprise a substantially cylindrical body and an inner cavity intended to receive the boat containing the sample, said body having substantially three parts, an upper part comprising an inner line communicating with said cavity and with the means for measuring the amount of hydrocarbon-containing products, a lower part comprising the opening of said cavity and a central part in which the boat will be placed, and the three parts can be surrounded by an electric heating element helically wound with contiguous pitches for the upper and the lower part and with a substantially double pitch for the central part.

The device can include means for feeding the boat into said heating means comprising means for measuring the temperature at the level of the boat and means of circulation of a non-oxidizing fluid, for example nitrogen or helium, or of an oxidizing fluid, for example air or oxygen.

The heating means can each comprise a temperature measuring means situated in the wall of the central part of said body, substantially at the level of the boat.

The device can include means for regulating and for programming the temperature of the heating means controlled by said temperature measuring means of said feed means, and said regulation and programming means can be controlled by said temperature measuring means situated in the wall of the central part of said body when the boat is outside the heating means, the latter then being open.

The means of heating in a non-oxidizing atmosphere can include a means for sweeping the inner cavity of the heating body with a non-oxidizing fluid when said body is open.

The device can comprise means for moving the boat between the two heating means and a storage support, comprising an arm equipped with a boat clamp, said arm being controlled in rotation in order to move a boat into one, of the three positions and in height to seize or to put the boat down, and the storage support can have the shape of a rotary tray on which various boats are arranged in a circle.

The device can comprise a first pair of cells for measuring continuously the $CO_2$ and the CO contained in the effluent released by the first heating means and a second pair of cells for measuring continuously the $CO_2$ and the CO contained in the effluent released by the second heating means.

The device can comprise electronic interface means between the measuring means, the valve or distributor control means, the temperature regulation means, the boat displacement means, and a computer comprising storage and visual display means.

The invention relates to a system of petroleum evaluation from geologic sediment samples. The system includes:

a device as described above, a PC type computer interfaced with said device and comprising visual display, print and working parameters entry peripherals, the computer comprising a multi-task software including a menu offering several preprogrammed analysis cycles that can be carried out by means of said device, among which: the mother rock analysis cycle, the kerogen or coal analysis cycle, the analysis cycle for determining the kinetic parameters of the degradation of an organic matter, the reservoir rock analysis cycle, the maturation preparative analysis cycle.

The multi-task software allows real-time display of characteristic measurements or curves, said software comprising means for changing the selected cycle in progress according to the characteristic measurements or curves obtained.

BRIEF DESCRIPTION OF THE DRAWINGS

Other features and advantages of the present invention will be clear from reading the description hereafter, given by way of non limitative examples, with reference to the accompanying drawings in which.

DESCRIPTION OF THE INVENTION

The principle of the method is described hereafter. A rock sample or a concentrated organic matter sample is subjected to a programmed heating law, first in an inert atmosphere, then with an oxidizing gas so that each analyzed product release corresponds to the real temperature of the sample at the time of its production. The effluents are analyzed continuously by means of a flame ionization detector (FID) for the hydrocarbons released, and of an infrared device (IR) for the $CO_2$ and the CO produced by cracking of the organic matter or decomposition of the carbonates.

The various curves are thereafter integrated and interpreted in order to obtain the first analysis results:

the amount of free hydrocarbons (peak S1, FIG. 3A), the petroleum potential (peak S2, FIG. 3A), the Tmax (maximum temperature at the top of the pyrolysis peak), the amounts of $CO_2$ and of CO (peaks S3 and S3', FIG. 3A) obtained while cracking organic matter in determined temperature ranges. The vertices of the curves are given in true temperature thanks to the continuous measuring device, the carbon residue is determined by the amounts of $CO_2$ and of CO obtained during the oxidation of the pyrolysis residue (peaks S4 and S4', FIG. 3B). The vertices of each curve are also determined in true temperature, the inorganic carbon is generally obtained by peak S5 and S3" corresponding to the decomposition of calcite and of dolomite. The maximum $CO_2$ releases are noted to determine the composition of the carbonate. The minimum releases are determined to decompose peak S5 into different carbonates.

The conventional analysis parameters such as PI (production index), HI, OI, and other necessary ratios derived from the new functions will be deduced from these base elements.

The device according to the invention is made up of an automaton that performs the measurements and of a PC that controls the automaton, serves as an interface with other computers, manages the analyses, allows real-time visual display of the results and uses control and test softwares.

The measuring device comprises two micro-ovens, a sample changer supplying them with boats and an analysis system consisting of a flame ionization detector (FID) and of two infrared cells (IR). These elements are connected to electronics and to a fluid circuit managed by the PC and by the automaton software.

Figure 1:
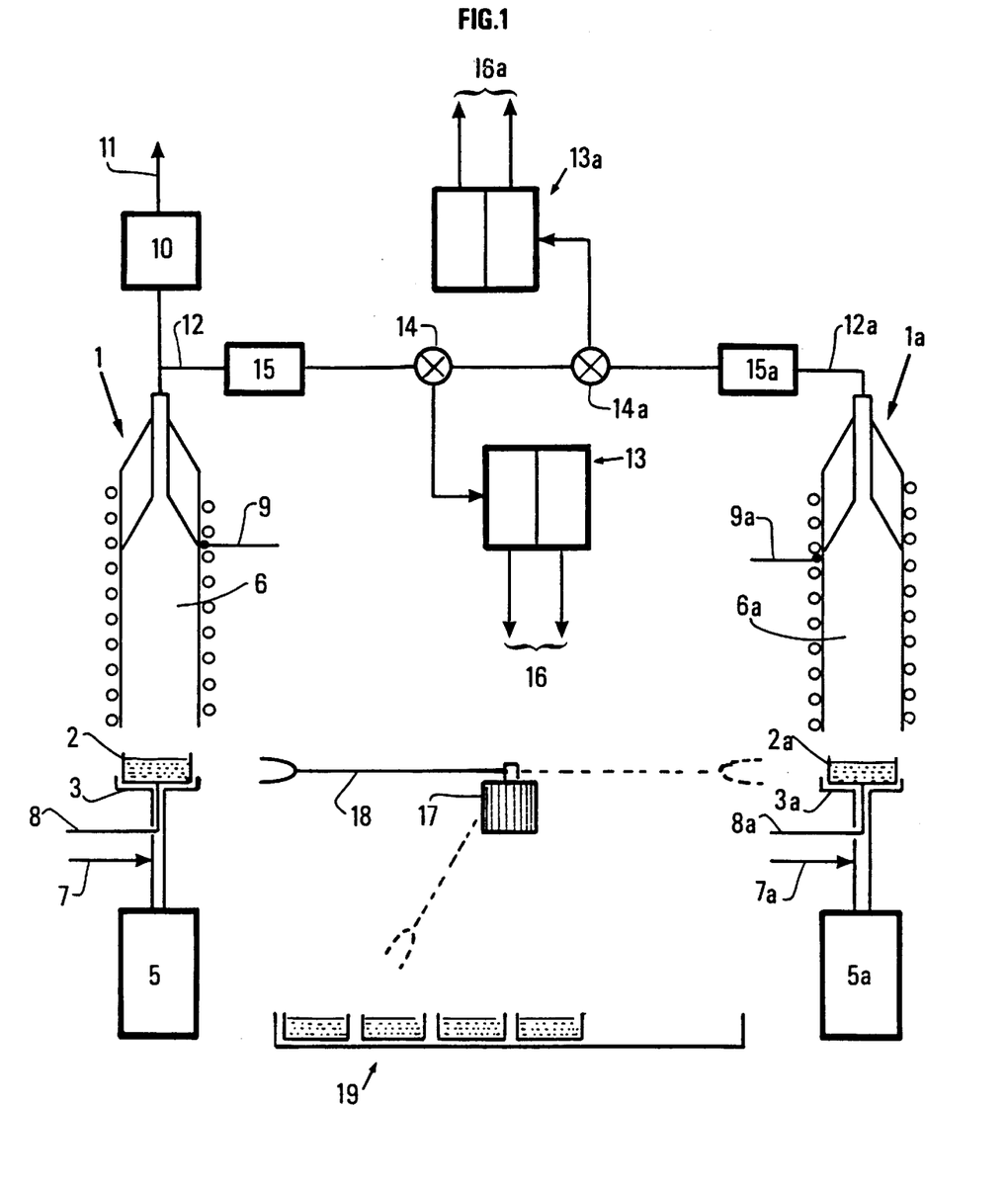
FIG. 1 shows the flowsheet of the measuring device.

FIG. 1 describes the improved pyrolysis and oxidation device according to the present invention. Reference number 1 shows the heating assembly suited for the pyrolysis of sample 2 placed in a boat 3 borne by a piston 4. Displacement means 5 for moving the boat feed the sample into the inner space 6 of the oven. The displacement means can be pneumatic, hydraulic or electric jacks. Reference number 7 schematizes the line delivering the carrier fluid for sweeping the products pyrolysed in the oven. This fluid (nitrogen or helium) sweeps the sample by flowing through the piston. Distribution means (not shown) lead the carrier fluid to the upper part of the oven to perform a back-sweeping drain of the inside of the oven when the piston moves back, for example at the end of the pyrolysis process in order to transfer the sample and/or to load another sample. In fact, the influence of oxygen on the organic deposits on the walls of the pyrolysis oven can generate oxygen compounds $CO_2$ and CO that can hinder the analysis.

A temperature probe 8 measures the temperature at the level of the boat bottom, thus very close to the sample. The measuring point of another temperature probe 9 is in the wall of the well, at the level of the upper position of the boat, a position corresponding to the optimum heating point. The temperature programming of the oven is preferably performed by means of probe 8, which allows good control and knowledge of the pyrolysis temperature of the sample. Temperature probe 9 is used to check the temperature of oven 1 when the oven is open and piston 4 has moved down to extract boat 3 and to replace it by another. The temperature of oven 1 can thus be maintained at a value close to the value determined for the next pyrolysis, which prevents too great a heat loss.

Heating assembly 1A is similar to heating assembly 1 in every respect. This assembly 1A is intended for the operation of oxidation of a sample, generally after pyrolysis. The identical elements are referred to as "A". It may be noted that the fluid injected through line 7A is air in this case.

Heating assemblies 1 and 1A both have temperature regulation means allowing the temperature gradient to be programmed, and the temperature can reach or even exceed 850° C.

Reference number 10 represents the flame ionization detector FID delivering a signal S representative of the amounts of hydrocarbon-containing products released from the sample during heating. Arrow 11 shows the transfer of signal S to the digitizing means. The flame ionization detector FID must withstand high temperatures, and it therefore requires joints withstanding such conditions without creeping or desorbing products that might cause the base line to drift.

The linearity and the sensitivity thereof, combined with a very slight base line drift, guarantee high precision in the analysis of hydrocarbons.

The analog signal will be digitized and smoothed with the maximum number of points depending on the programming rate.

Line 12 leads part of the flow to means 13 intended for continuous analysis is of the amounts of $CO_2$ and of CO produced by pyrolysis of the sample. At the outlet of the pyrolysis oven, the divided flow is heated to at least 360° C. in order to prevent heavy product condensations.

Line 12A leads at least part of the oxidation flow to means 13A intended for continuous analysis of the amounts of $CO_2$ and of CO produced.

Distribution means 14 and 14A allow to use only one or other of the $CO_2$ and CO analysis means for the pyrolysis or oxidation flow. Preferably, for operational time saving reasons, means 13 and 13A will be allocated to only one heating means. The continuous analysis means are for example infrared detectors.

The infrared cells IR, being specific to a gas, can measure continuously the $CO_2$ and CO concentrations in the effluents during pyrolysis and oxidation. They allow to win access to new information such as the presence and the amount of various carbonates, the maximum release temperatures, the peak shapes, the transition between the inorganic carbon and the organic carbon and the distribution of each oxygen compound in the various cracking reactions of the organic matter.

The length of the measuring cells depends on the maximum sensitivity required, therefore on the minimum concentration to be measured. It depends on the amounts of $CO_2$ and CO produced by the sample (therefore on its mass), on the analysis time (therefore on the heating conditions) and on the flow rate of the carrier gas that is a diluting factor.

* The cell analyzing the $CO_2$ measures maximum concentrations of 2% for a flow rate ranging from 50 to 200 ml. This bracket is linearized on four automatic-change ranges:

range 1:0 to 2% $CO_2$
  range 2:0 to 1% $CO_2$
  range 3:0 to 0.5% $CO_2$
  range 4:0 to 0.25% $CO_2$

* The cell analyzing the CO measures maximum concentrations of 1% under the same conditions as cell $CO_2$. The 4 ranges are:

range 1:0 to 1% CO
  range 2:0 to 0.5% CO
  range 3:0 to 0.25% CO
  range 4:0 to 0.125% CO.

The signals obtained from cells IR are re-shaped in order to obtain curves with the same attenuation, digitized like the FID signal.

The device further comprises flow purification means 15 and 15A

Arrows 16 and 16A refer to the transfer of measurements to the electronic digitizing means, and to an electronic interface between the measuring components, a valve or distributor control, a temperature regulation means, a boat displacement component and a computer comprising storage and visual display means. The device can be coupled to programmable electronic apparatus which allows real-time display of characteristic measurements, said software allowing changing the selected cycle in progress according to the characteristic measurements or curves obtained.

Furthermore, the device includes a sample changer 17 whose arm 18 is suited to shift the boat containing a sample between three possible positions: the pyrolysis oven, the oxidation oven and storage support 19.

The sample changer has simplified mechanics so that displacements can be performed by means of electric stepping motors. Any control possibilities are thus available and they only depend on the working software. For example, it will be possible to load the boats only in the oxidation oven for particular studies. Another possible application will consist in subjecting the samples to a heat treatment in an oven and in recovering them afterwards on the boat or storage support (19) to analyze them according to the desired Rock-Eval cycle.

The boat support is not linear but circular: it exhibits the shape of a carousel, which saves space and allows quicker access to the desired boat bit means of a forward or reverse motion of the changer. A number assigned to each location allows passage of the samples to be programmed in the chronological positioning order of the boats on the changer as well as according to either the various cycle or analysis types or to analysis priorities.

Figure 2:
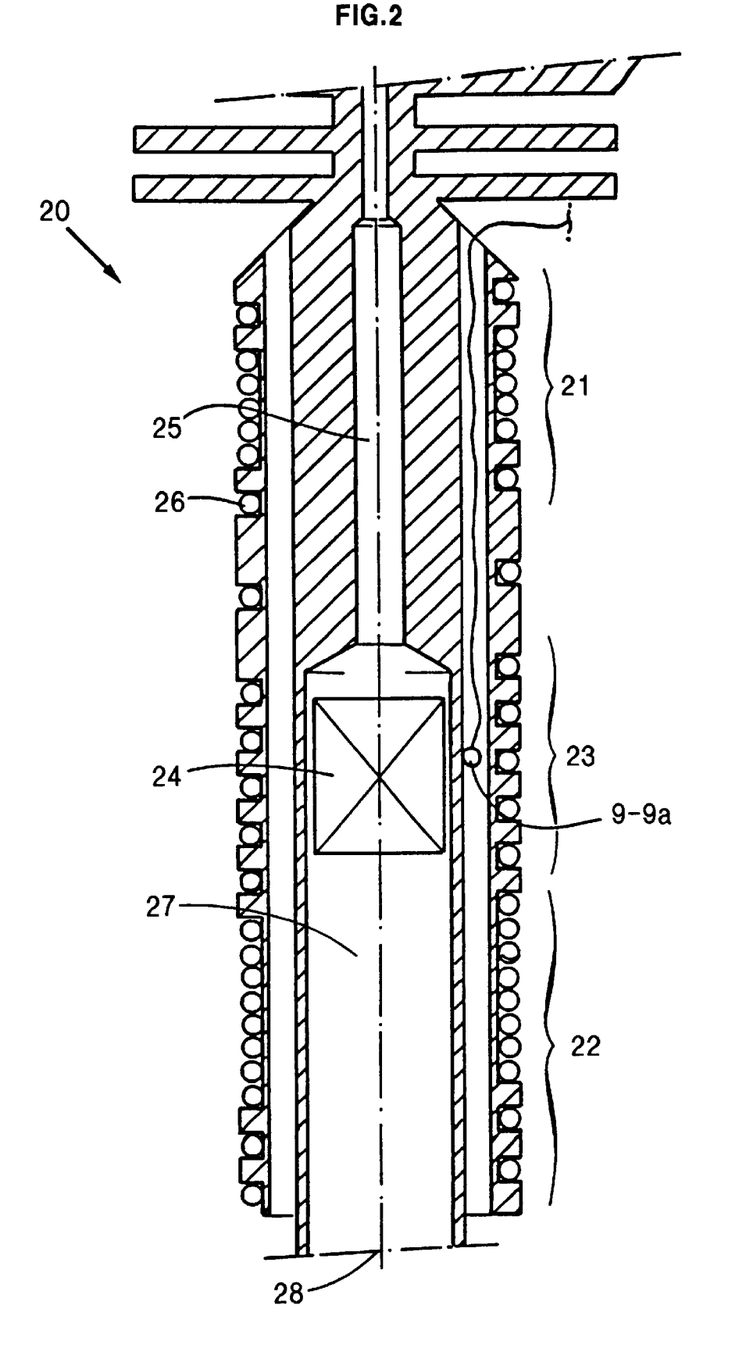
FIG. 2 shows the principle of the heating elements.

FIG. 2 shows the particular structure of the pyrolysis and oxidation ovens. Optimization of the heating elements is necessary to obtain temperatures at least above 850° C. and an initial temperature of at least 100° C., good linearity of the imposed heat gradients, energy saving and a sample temperature very close to the set value.

Oven 20 has a tubular shape and comprises three main parts: two end parts 21, 22 and a central part 23 at the level of which the sample is placed in testing position as shown by reference number 24.

The ovens include a substantially cylindrical body and an inner cavity (27) intended to receive the boat containing the sample, said body having substantially three parts, an upper part comprising an inner line (25) communicating with said cavity and with the means for measuring the amount of hydrocarbon-containing products, a lower part (22) comprising the opening (28) of said cavity and a central part (23) in which the boat will be placed, and in that the three parts are surrounded by an electric heating element (26) helically wound with a given pitch for the upper and the lower parts and with substantially double said given pitch for the central part.

The inner space of the tube forming oven 20 has a reduced diameter 25 at the level of the downstream end of the oven with respect to the direction of circulation of the carrier flow of the pyrolysis or oxidation effluents. The winding of the electric heating resistor 26 is optimized as follows: the resistor is mainly wound with contiguous pitches in the two end parts 21 and 22, whereas in central part 23 the winding pitch is greater, for example doubled. The resistor heals the body of the oven by contact and contact can be improved by embedding the resistor in a metal alloy. The temperature measuring point of thermocouple 9 or 9A is as close to the inner wall of the oven as possible, at the level of area 24.

The ovens thus structured show the advantageous characteristics as follows:

the initial Ti and end temperatures Tf range between 100 and 900° C., the heating program is a multi-slope program. One or more program segments can be introduced between Ti and Tf, that can be variable-duration isotherms or gradients whose rates range from 0.2° C./min to 50° C./min, temperature being the reference during analysis, signals corresponding to well-defined temperatures are used to perform switching or connecting operations. The temperature rise curve will be associated with all the analysis curves, the thermal inertia and the power required being low, the initial temperature Ti can be lowered and cooling of the ovens is facilitated with a view to a fast return to the initial temperature.

Volatilization of the lightest free hydrocarbons (lower than $C_5–C_6$) contained in a rock can thus be carried out at low temperature (about 100° C.). Separation of the constituents will then be prompted according to the boiling point thereof by means of a suitable temperature programming. This technique can be applied either to the study of mother rocks or to the study of reservoir impregnations.

The possibility of carrying out pyrolysis up to about 850° C. allows to obtain, notably for some samples, complete volatilization or degradation of the residual organic matter contained in mother rocks or in reservoir rocks ($C_6$ to $C_{40}$ hydrocarbons, resins and asphaltenes). The petroleum potential of the sample is increased, in some cases, by a non-negligible amount in relation to a conventional pyrolysis at 600° C., which gives a more representative HI.

Furthermore, the kinetic parameters of the organic matters of terrestrial origin, determined by means of pyrolysis, are more precise when the adjustment pyrolysis curves return to the base line (case of the curves obtained from high-velocity progammings).

High-temperature pyrolysis is also of use for determining the high maturities of mother rocks by means of the Tmax scale. In fact, conventional pyrolysis up to 650° C. gives, for some mature rocks, a peak S2 that represents only the cracking start without reaching the peak maximum. On the other hand, high-temperature pyrolysis gives Tmax values above about 587° C. thanks to a complete, pyrolysis of the sample.

A programmed oxidation temperature that can reach 850° C. instead of the isothermal heating at 600° C. currently used allows the most resistant cokes to be burned. It is then possible to measure all the residual carbon, even in the difficult case of very mature mother rocks (case of highly advanced coals). The TOC values are then more accurate and quite comparable to the values obtained by combustion at 1,500° C. in a LECO type device or with the conventional elementary analysis method.

High-temperature oxidation is necessary to decompose carbonates such as calcite and dolomite, which can only be done at temperatures about 600° C. The total inorganic carbon of the rocks (by taking account of the siderite contained in curve S3) and different carbonate varieties can thus be accessed.

Figures 3A, 3B:
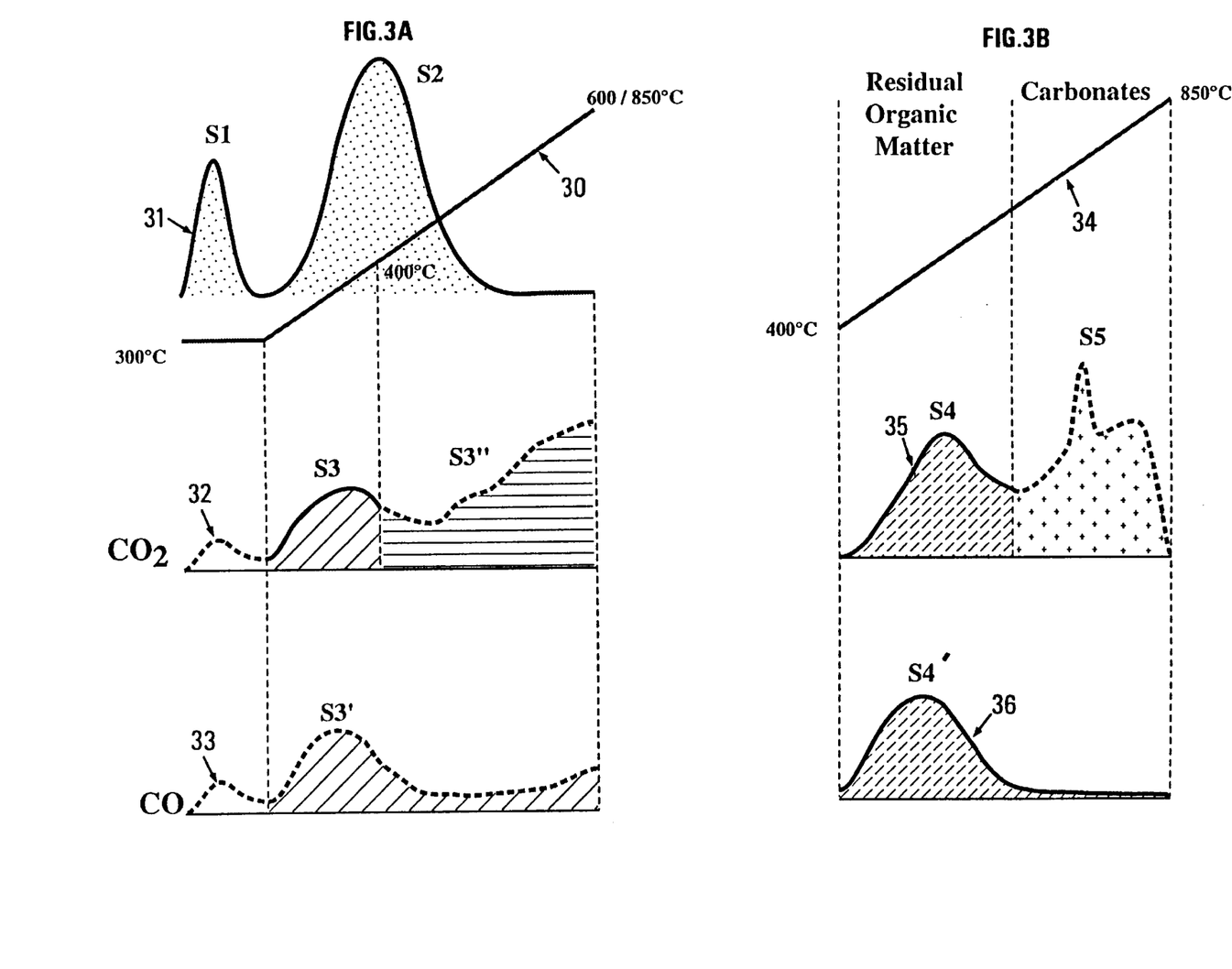
FIGS. 3A and 3B show typical records obtained with the present device.

FIGS. 3A and 3B show typical measurements performed with the device described in FIG. 1.

The graphs of FIG. 3A relate to measurements and recordings performed is during the pyrolysis of a sample. The graphs of FIG. 3B relate to measurements and recordings performed during the oxidation of the sample, after pyrolysis.

In FIG. 3A, curve 30 represents the temperature to which the sample was subjected. In this example, an isothermal plateau is achieved at 300° C., followed by a temperature increase according to a determined gradient so as to reach, at the end of the pyrolysis, a maximum temperature of 850° C.

Curve 31 represents the signal recorded by detector FID. It comprises a first peak S1 corresponding to the volatilization of the free hydrocarbons during the isothermal stage and a peak S2 corresponding to the pyrolysis of kerogen. According to the nature of the sample and to the temperature gradient used, two peaks S2a and S2b can be distinguished. This measurement principle is described in document FR-9,408,383.

Curves 32 and 33 correspond respectively to the amount of $CO_2$ and of CO produced by the sample subjected to the temperature law of curve 30. Curves 32 and 33 are provided by continuous $CO_2$ and CO measuring means, for example infra-red detectors specifically suited to the present device. A peak S3, S3' and S3" can be seen here, that will be explained hereinafter.

Continuous measuring and reading, during pyrolysis, of the $CO_2$ content allows to differentiate peak S3 from peak S3", the latter corresponding to inorganic carbon. Furthermore, continuous measurement of the CO content complements the measurement of $CO_2$, and increases the calculation precision and the representativity of the various petroleum indices.

In FIG. 3B, curve 34 shows the law of programming of the oxidation temperature gradient. In fact, according to the present invention, the temperature of the oxidation oven is programmable, which allows to obtain peaks S4, S5 and S4" continuously and as a function of the temperature. Curve 35 corresponds to the measurement of the $CO_2$ content, curve 36 corresponds to the continuous measurement of the CO content.

Figure 4:
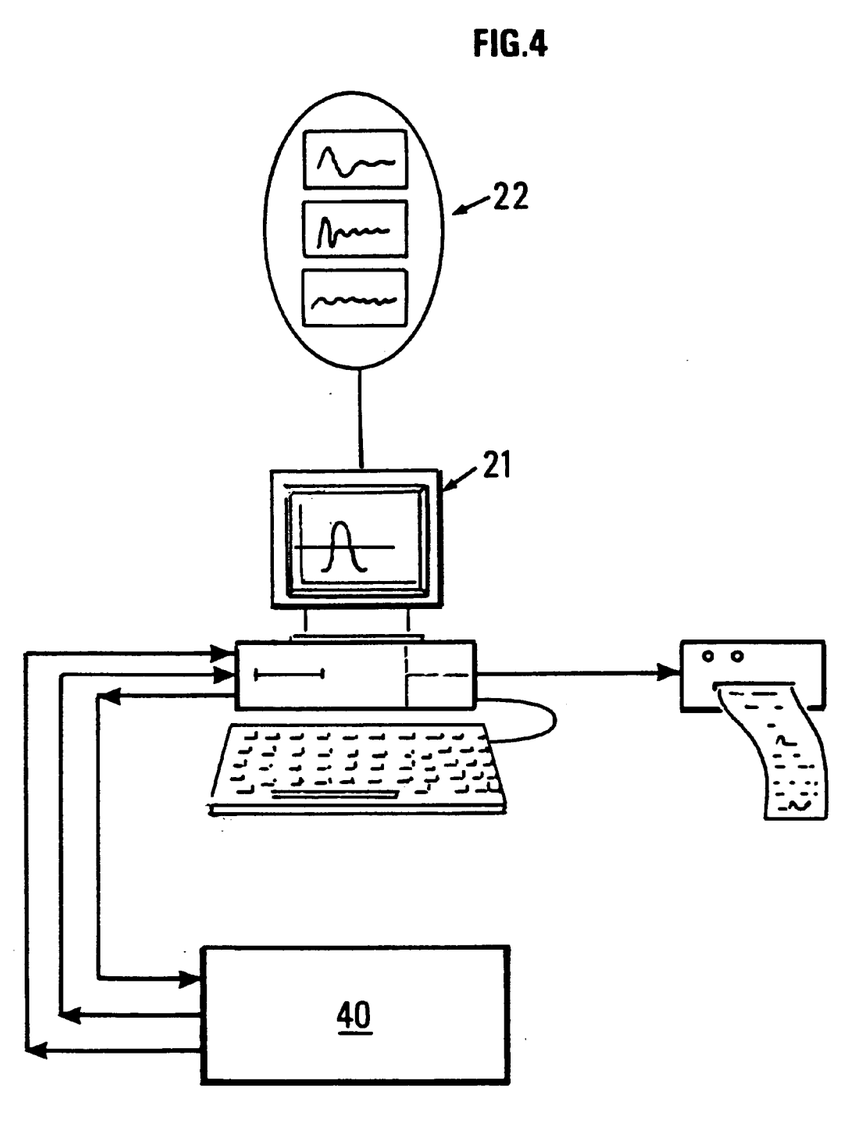
FIG. 4 diagrammatically shows the petroleum evaluation assembly.

FIG. 4 shows the general architecture of the system of petroleum measurement and evaluation from a sample.

Reference number 40 represents the measuring automaton, the ovens and the various signal sensors, as described in FIGS. 1 and 2. Reference 21 represents a computer, for example of the PC type, comprising a central processing unit and a display screen. The control and acquisition software is of the WINDOWS type allowing the user to readily select the desired analysis type and cycle, and to follow the progress of the analysis on a screen. Table 22 shows the various analysis types that can be used by the automaton type according to the present invention. The measuring assembly allows to view and to process the results during acquisition of new measurements. Curve or table printouts or on-screen displays, partial data processing and entry of or modifications to the parameters of new analyses are highly time-saving for the operator.

The computer comprises several softwares for managing various types of analyses, for example listed hereunder under trademarks registered by IFP:

ROCKSIX: Rock-Eval data acquisition and determination of true pyrolysis temperatures ROCKINT: interpretation of these data after correction and complementary data input OPTKIN: determination of the kinetic parameters of mother rocks MATOIL: hydrocarbon maturation and generation model GENEX: hydrocarbon generation and expulsion model by carbon classes.

Four broad types of analyses can be defined according to the category of the samples to be processed (raw rocks, pure kerogens and organic matters, reservoir samples), or according to the results necessary and useful for the user (pyrolyses for determining kinetic parameters (OPTKIN), preparative pyrolyses with various heating plateaus and gradients, particular processings, etc.). The commonest type of analysis is the conventional Rock-Eval analysis processing the rock samples according to criteria defined in the documents mentioned above. Analysis of the concentrated organic matter allows to obtain the complete carbon balance of the sample, in pyrolysis as well as in oxidation. The analysis referred to as OPTKIN allows samples to be pyrolysed at different velocities in order to obtain curves that will be processed thereafter by the software bearing the same name. Analysis of the reservoirs and of the tar mats fractionates the light and heavy compounds contained in a reservoir sample. The maturation preparative analysis serves to heat a mother rock sample for example under precise temperature conditions (isothermal or in temperature programming mode). During heating, the products released are measured. The sample is thereafter processed by pyrolysis and oxidation according to the use required for this maturation residue (OPTKIN or other analyses).

For each analysis type, a list of standard fixed cycles is offered. It can be completed by particular cycles predetermined by each user according to his needs and wishes.

The Conventional Rock-Eval Analysis

It is used to analyze mother rocks and to determine conventional Rock-Eval analysis parameters: amount of oil (S1), petroleum potential (S2), amount of oxygen compounds (S3), Tmax, TOC inorganic carbon, PI, HI and OI with a view to an interpretation or a selection of samples that will be subjected to more elaborate treatments.

In order to optimize the analysis duration according to the rocks to be processed and to the information required about the samples, the operator chooses in the various preprogrammed cycles or sets new parameters.

Concentrated Organic Matter and Coal Analysis

It is used to analyze kerogens, coals and all the other concentrated organic matters. High-temperature pyrolysis and oxidation provide the carbon balance of the sample. In this analysis, the source of the carbon present in the HC, $CO_2$ and CO compounds is only organic.

Pyrolysis at 750° C. gives the whole of peak S2. Oxidation of the residual matter with temperature programming up to 800° C. burns the cokes down (in the previous analyses, during programmed oxidation, integration of the $CO_2$ and CO curves ends at 650° C. and the surfaces obtained after this temperature are included in the carbonates heading).

According to the type of organic matter, the pyrolysis and oxidation conditions vary considerably. In order to optimize the analysis durations and also to allow a different processing of the curves obtained, different cycles are offered by the PC in the menu.

The Analysis Known as OPTKIN

To determine the kinetic parameters of the degradation of an organic matter, the OPTKIN software requires several pyrolysis curves obtained at different velocities with a factor of at least 8 between the highest velocity and the lowest velocity. The present invention allows to select the programming velocities within the 0.2° C./min-50° C./min range. Each velocity has a corresponding end temperature allowing the pyrolysis curve to return to its base line. For example, with a gradient of 50° C./min, an end temperature of 750° C. is required to obtain a complete cracking of the organic matter, whereas at 0.2° C./min cracking is completed at 450° C.

It may be seen that, with this new possibility, time savings are all the greater as the velocities are slower (25 h saved for the minimum velocity of 0.2° C./min and 15 min for a velocity of 50° C./min).

For each sample, the software imposes at least two curves and at most ten pyrolysis curves with extreme velocities exhibiting a ratio of 1 to 8 at the minimum. Each cycle thus allows to analyze at least ten times the same rock with variable velocities. According to the cycle used, the end temperature is determined by the velocity.

Reservoir and Tar-Mat Analysis

It allows to differentiate two peaks in the pyrolysis curve: a peak "S2$a$" corresponding to heavy hydrocarbons that have not been vaporized during the isothermal stage and a peak "S2$b$" that is the result of the cracking of resins and asphaltenes and of the organic matter present in the sample. The residues obtained after pyrolysis are oxidized to determine the total carbon.

Maturation Preparative Analysis

It allows to condition a sample in an inert gas stream at a temperature determined by an isotherm or in temperature programming mode. The residue is either processed immediately by pyrolysis and oxidation or recovered for a further use in another analysis according to the present invention, or used in another equipment of a different method.

We claim:

1. A device for determining $CO_2$ CO content in a geologic sediment sample placed in a boat, said device including a first heater for heating said sample in a non-oxidizing atmosphere, a measuring component communicating with said first heater for determining hydrocarbon-containing products released after feeding the sample into said first heater, a second subsequent heater communicating with said first heater heating said sample in an oxidizing atmosphere, a $CO_2$ measuring component for determining an amount of $CO_2$ contained in effluents discharged from said first and second heaters, said $CO_2$ measuring component includes at least one cell for measuring continuously the amount of $CO_2$ produced by pyrolysis of said sample during heating by said first and said second heaters and a measuring component determining an amount of CO contained in the effluents discharged from said first and second heaters.

2. The device as claimed in claim 1, wherein the first and the second heaters each comprise an identical oven and a programmable temperature controller regulating the temperature of the two ovens.

3. The device as claimed in claim 1, comprising a feeding component feeding the boat into said first and said second heaters, said component comprising a temperature measuring component measuring the temperature of said sample and a circulating component delivering a non-oxidizing or an oxidizing fluid to said sample.

4. The device as claimed in claim 1, comprising a transfer component moving the boat between said first and said second heaters and a storage support said transfer component comprising an arm equipped with a boat clamp, said arm being controlled in rotation in order to move a boat into one of three positions, to adjust height, to seize or to put the boat down, the storage support having the shape of a rotary tray on which various boats are arranged in a circle.

5. The device as claimed in claim 1, comprising a first pair of cells measuring continuously $CO_2$ and CO contained in said effluent discharge by the first heater and a second pair of cells for measuring continuously $CO_2$ and CO contained in said effluent discharged by the second heater.

6. The device as claimed in claim 1, comprising an electronic interface between the measuring component, a temperature regulation means, a boat displacement component and a computer comprising storage and visual display means.

7. The device as claimed in claim 2, wherein said ovens include a substantially cylindrical body and an inner cavity intended to receive the boat containing the sample, said body having substantially three parts, an upper part comprising an inner line communicating with said cavity and with the $CO_2$ measuring component, a lower part comprising the opening of said cavity and a central part in which the boat will be placed, and wherein the three parts are surrounded by an electric heating element helically wound with a given pitch for the upper and the lower parts and with substantially double said given pitch for the central part.

8. The device as claimed in claim 7, wherein said first and second heaters each comprise a temperature measuring component placed in the wall of the central part of said body, said temperature measuring component measuring the temperature of each of said heaters.

9. The device as claimed in claim 7, wherein said first heater comprises a carrier fluid line sweeping the sample with a non-oxidizing fluid.

10. A system allowing petroleum evaluation from geologic sediment samples, comprising:

a device as described in claim 1, a computer interfaced with said device and comprising visual display, print and working parameter entry peripherals, said computer comprising multi-task software including a menu offering preprogrammed analysis cycles that can be performed by means of said device, including a mother rock analysis cycle, a kerogen or coals analysis cycle, an analysis cycle for determining kinetic parameters of degradation of organic matter, a reservoir rock analysis cycle, and a maturation preparative analysis cycle, said device supplying to said computer data input used in said analysis cycle.

11. The system as claimed in claim 10, wherein the software allows real-time display of characteristic measurements, said software allowing changing the selected cycle in progress according to the characteristic measurements obtained.

\* \* \* \* \*